(12) United States Patent
Cui et al.

(10) Patent No.: US 10,684,112 B2
(45) Date of Patent: Jun. 16, 2020

(54) STRUCTURE FOR MONITORING STABILITY OF EXISTING SUBGRADE/SLOPE AND CONSTRUCTION METHOD THEREOF

(71) Applicant: SHANDONG UNIVERSITY, Jinan, Shandong (CN)

(72) Inventors: Xinzhuang Cui, Jinan (CN); Weidong Cao, Jinan (CN); Lei Zhang, Jinan (CN); Junwei Su, Jinan (CN); Yilin Wang, Jinan (CN); Jun Li, Jinan (CN); Sheqiang Cui, Jinan (CN); Zhongxiao Wang, Jinan (CN)

(73) Assignee: SHANDONG UNIVERSITY, Shandong (CN)

( * ) Notice: Subject to any disclaimer, the term of this patent is extended or adjusted under 35 U.S.C. 154(b) by 178 days.

(21) Appl. No.: 16/074,647

(22) PCT Filed: Sep. 29, 2017

(86) PCT No.: PCT/CN2017/104484
§ 371 (c)(1),
(2) Date: Aug. 1, 2018

(87) PCT Pub. No.: WO2019/056410
PCT Pub. Date: Mar. 28, 2019

(65) Prior Publication Data
US 2019/0178623 A1   Jun. 13, 2019

(30) Foreign Application Priority Data
Sep. 22, 2017   (CN) .......................... 2017 1 0864496

(51) Int. Cl.
*G01B 7/16* (2006.01)
*E02D 17/20* (2006.01)
*G01N 33/24* (2006.01)

(52) U.S. Cl.
CPC ............... *G01B 7/16* (2013.01); *E02D 17/20* (2013.01); *E02D 17/202* (2013.01); *G01B 7/18* (2013.01); *G01N 33/24* (2013.01)

(58) Field of Classification Search
None
See application file for complete search history.

(56) References Cited

U.S. PATENT DOCUMENTS

| | | | | | |
|---|---|---|---|---|---|
| 5,823,709 | A | * | 10/1998 | Maher ..................... | E02B 3/122 405/20 |
| 5,911,539 | A | * | 6/1999 | Egan ....................... | E02B 3/122 405/16 |

(Continued)

FOREIGN PATENT DOCUMENTS

| CN | 204085568 U | 1/2015 |
|---|---|---|
| CN | 105115387 | 12/2015 |

(Continued)

OTHER PUBLICATIONS

Jun. 1, 2018 International Search Report issued in International Patent Application No. PCT/CN2017/104484.

(Continued)

*Primary Examiner* — Natalie Huls
*Assistant Examiner* — Jermaine L Jenkins
(74) *Attorney, Agent, or Firm* — Oliff PLC

(57) ABSTRACT

The structure has a subgrade or slope to be monitored and strip-shaped smart geosynthetic material compound devices. The strip-shaped smart geosynthetic material compound devices are buried to run through a subgrade or slope predicted slip crack surface. Gaps between the strip-shaped smart geosynthetic material compound devices and borehole inner walls are filled so that the force environment of the strip-shaped smart geosynthetic material compound devices is close to the subgrade or slope internal environment. Each strip-shaped smart geosynthetic material compound device (Continued)

has a strip-shaped geogrid, lead, and heat shrinkable tube. The lead is arranged in a length direction of the geogrid, and the lead and geogrid are fixedly connected at an interval of a set distance, with each fixed point forming a measuring point. The geogrid is wrapped in the heat shrinkable tube, and a free end of the lead is drawn out of the heat shrinkable tube.

7 Claims, 4 Drawing Sheets

(56) References Cited

U.S. PATENT DOCUMENTS

| | | | | |
|---|---|---|---|---|
| 5,975,810 | A * | 11/1999 | Taylor | E02D 29/0225 |
| | | | | 405/262 |
| 6,595,726 | B1 * | 7/2003 | Egan | E02D 29/0241 |
| | | | | 405/262 |
| 7,083,364 | B2 * | 8/2006 | Kim | E02D 29/0225 |
| | | | | 405/284 |
| 9,556,579 | B2 * | 1/2017 | Ahlberg | E02D 3/00 |
| 9,556,580 | B2 * | 1/2017 | Walsh | E01C 11/16 |
| 2002/0069605 | A1 * | 6/2002 | Hong | E02D 29/0241 |
| | | | | 52/660 |

FOREIGN PATENT DOCUMENTS

| | | |
|---|---|---|
| CN | 204944376 U | 1/2016 |
| CN | 105953737 A | 9/2016 |
| CN | 106960548 A | 7/2017 |
| CN | 207335617 U | 5/2018 |
| KR | 10-1668788 B1 | 10/2016 |

OTHER PUBLICATIONS

Jun. 1, 2018 Written Opinion issued in International Patent Application No. PCT/CN2017/104484.

\* cited by examiner

STRUCTURE FOR MONITORING STABILITY OF EXISTING SUBGRADE/SLOPE AND CONSTRUCTION METHOD THEREOF

FIELD OF THE INVENTION

The present invention belongs to the field of civil engineering and particularly relates to a structure for monitoring the stability of an existing subgrade/slope and a construction method thereof.

BACKGROUND OF THE INVENTION

In recent years, with the large-scale construction of infrastructures, some high-fill subgrade slopes and high cutting slopes have emerged, which include rock slopes and soil slopes. Slope hazards caused by natural landslides, debris flows and human engineering activities have brought great losses to the economic construction and people's life and property. Therefore, the stability analysis of slopes is of great significance to the safety protection of slope engineering. At present, there are many methods for monitoring the stability of slopes, such as displacement monitoring, GPS monitoring, underground sound measurement and hydrologic monitoring methods and the like, but some of these methods may be relatively simple in means and low in precision, while some may be costly and uneconomical. Now, a smart geosynthetic material is being increasingly utilized in road engineering, which has the advantages of high precision, low cost and the like. For a newly built subgrade and/or slope, the smart geosynthetic material can be buried in the subgrade and/or slope in layer-by-layer laying and layer-by-layer rolling manners, and then the stability of the subgrade and/or slope can be monitored. However, an existing subgrade and/or slope cannot be monitored by this method.

SUMMARY OF THE INVENTION

In view of the technical problems existing in the prior art above, an objective of the present invention is to provide a structure for monitoring the stability of an existing subgrade/slope and a construction method thereof. According to the present invention, the pulling sensitive characteristic of a smart geosynthetic material is exploited in projects such as existing subgrades, slopes, and retaining walls, so that the stability of these works can be monitored, thereby solving the problem that the stability of existing subgrades/slopes cannot be monitored using the smart geosynthetic material.

To solve the above technical problem, the following technical solutions are adopted in the present invention.

A structure for monitoring the stability of an existing subgrade/slope comprises a subgrade or slope to be monitored and a plurality of strip-shaped smart geosynthetic material compound devices.

A plurality of vertical boreholes are drilled in a width direction of the subgrade or slope, or a plurality of transverse boreholes are drilled in a vertical direction thereof. One strip-shaped smart geosynthetic material compound device is buried in each vertical borehole or transverse borehole so deep as to run through a predicted slip crack surface of the subgrade or slope. A gap between the strip-shaped smart geosynthetic material compound device and the inner wall of the borehole is filled tightly so that the force environment of the strip-shaped smart geosynthetic material compound device is close to the internal environment of the subgrade or slope.

The strip-shaped smart geosynthetic material compound device comprises a geogrid, a lead, and a heat shrinkable tube. The geogrid is strip-shaped. The lead is arranged in a length direction of the geogrid, and the lead and the geogrid are fixedly connected at an interval of a predetermined distance, with each fixed point forming a measuring point. The geogrid is wrapped in the heat shrinkable tube, and a free end of the lead is drawn out of the heat shrinkable tube.

As used herein, "existing" means already existing, i.e., already existing, already built subgrades/slopes.

Geogrid: a grid which is a two-dimensional grid or a three-dimensional screen grid having a particular height formed from a high polymer such as high polyethylene and polyvinyl chloride through hot molding or mold pressing, the grid becoming the geogrid when used in civil engineering.

Heat shrinkable tube: a heat shrinkable tube made from a polyolefin material and having the functions of shrinkage at high temperature, flexibility, flame retardance, insulation, and corrosion prevention.

Conductive adhesive: an adhesive having particular electrical conductivity after being cured or dried.

According to different situations, holes may be selectively drilled in a width direction or a vertical direction of the subgrade or slope. The strip-shaped smart geosynthetic material compound devices are inserted into the boreholes and run through the predicted slip crack surface. When the subgrade or slope slips or tends to slip, the strip-shaped smart geosynthetic material compound devices may become deformed to generate corresponding signals. The monitoring structure is simple in and has good accuracy and sensitivity of monitoring.

When the drilling direction is set to be a transverse (horizontal) or vertical (perpendicular) direction, the strip-shaped smart geosynthetic material compound devices are perpendicular to the direction of force acting thereon, and thus are more likely to deform to generate signals.

The geogrid is wrapped in the heat shrinkable tube so that the smart geosynthetic material can be effectively prevented from being affected by water in soil.

The free end of the lead is drawn out so that the lead can be connected to a data acquisition instrument. The data acquisition instrument can monitor a resistance value at each measuring point to facilitate subsequent data analysis.

Further, the lead and the geogrid are bonded by a conductive adhesive and fixed using an adhesive tape at each measuring point.

The deformation of the soil mass may be analyzed by monitoring changes of resistance values due to the effect of loads on the geogrid. To measure the resistance values more accurately, the geogrid is wrapped using the conductive adhesive. Further, a distance between every two adjacent measuring points is 0.5-1 m.

Still further, each measuring point is fixed in a middle position of the geogrid. The purpose of fixing each measuring point in a middle position is to allow each measuring point to be located on the same force-bearing section, so that errors of measured data can be reduced as much as possible.

Still further, the lead between every two adjacent measuring points is pulled tight. When the lead is pulled tight, the geogrid may become deformed under a force, and the lead may become deformed accordingly, which can improve detection sensitivity.

Further, the width of the strip-shaped smart geosynthetic material compound device may be 5-10 cm, and the length thereof may be determined as required.

Further, the heat shrinkable tube belongs to that with adhesive and is of a double-layer structure with an outer layer made from a polyolefin alloy material and an inner layer made from a hot melt adhesive.

The hot melt adhesive is a plastic adhesive, and the physical state thereof may change with temperature within a particular temperature range.

The polyolefin alloy material has the advantages of flexibility, shrinkage at low temperature, insulation, corrosion resistance, and wear resistance, and the inner layer has the advantages of low melting point, good adhesive force, good waterproofing and sealing properties, and the like. The geogrid and the lead are wrapped in the adhesive-containing heat tube. After being heated to 84-120° C., the adhesive-containing heat tube may shrink, and the hot melt adhesive of the inner layer is melted so that the geogrid and the lead are wrapped therein tightly.

Further, a distance between every two adjacent boreholes is 1-2 m.

Further, the diameter of each borehole is 8-15 cm.

A system for monitoring the stability of an existing subgrade/slope comprises the above structure for monitoring the stability of an existing subgrade/slope and a data acquisition instrument. The lead of the monitoring structure is connected to the data acquisition instrument.

A construction method of the above structure for monitoring the stability of an existing subgrade/slope comprises the following steps:

1) A plurality of vertical boreholes are drilled in a width direction of the subgrade or slope, or a plurality of transverse boreholes are drilled in a vertical direction thereof.

2) A strip-shaped smart geosynthetic material compound device is nested into a plastic tube and then fed into each borehole as far as it runs through a predicted slip crack surface of the subgrade or slope.

3) A gap between the borehole and the strip-shaped smart geosynthetic material compound device is filled. During filling, the plastic tube is slowly taken out. The plastic tube is taken out a corresponding distance once the gap is filled by 1.5-2.5 m, until the gap is completely filled. In the filling process, it is ensured that the bottom of the plastic tube is immersed in fillers.

4) A lead in of the smart geosynthetic material compound device is drawn out, and then is connected to a data acquisition instrument. A resistance value at each measuring point is measured. Two adjacent measurement points with the maximal resistance difference are found out. Then, the position and orientation of a slip crack surface of soil mass are determined and the evolution process of the slip crack surface is monitored.

Further, when the subgrade or slope is a high subgrade or high slope, transverse boreholes are drilled in the vertical direction thereof at intervals of 1-2 m.

Alternatively, when the subgrade or slope is a wide subgrade or wide slope, vertical boreholes are drilled in the width direction thereof at intervals of 1-2 m.

A high slope is a soil slope which is more than 20 m and less than 100 m high, or a rock slope which is more than 30 m and less than 100 m high. When the height of a soil slope is less than 20 m or the height of a rock slope is less than 30 m, it is deemed to be a wide slope. Subgrades can be classified in the same way.

Further, in step 3), different materials are chosen to fill gaps with respect to different soil slopes or subgrades.

Still further, M20 cement mortar having a cement-mortar ratio of 1:1 is used for gap filling for soft rock or decomposed rock slopes or subgrades.

M30 cement mortar having a cement-mortar ratio of 1:1 is used for gap filling for hard rock slopes or subgrades.

Bentonite slurry is used for gap filling for soft soil slopes or subgrades, where the mass ratio of water:bentonite:alkali:cellulose in the bentonite slurry is 1000:(60-100):(2-5):(2-5).

Cement soil is used for gap filling for hard soil slopes, where bentonite is selected as soil; the mass percentage of the mixed cement is 10%-15%, and a water-cement ratio of cement slurry is 1.

Principles

The smart geosynthetic material is an electrically conductive composite material. The conducting behavior of the electrically conductive composite material generally presents a typical percolation phenomenon. A sensitive material has the functions of sensing and driving and may exhibit some special effects after being specially designed, such as a pulling sensitive effect which refers to a process where the electrical conductivity changes under the action of external pull. The occurrence of the pulling sensitive effect is due to that the electrically conductive path is partially damaged and thus in a high-impedance state when the deformation of the composite material exceeds a critical value.

With regard to the strip-shaped smart geosynthetic material compound device in the present invention, when an external force is applied thereto, the material itself becomes deformed, and two adjacent measuring points at the deformation position of soil mass will have significant changes in electrical resistivity. In this case, two measuring points having the most significant change in electrical resistivity can be found out from the acquired real-time data, thereby the position and the orientation of the slip crack surface of soil mass and the evolution process of the slip crack surface can be analyzed and determined.

Advantages of the Present Invention

1. The stability of existing subgrades and slopes can be monitored by using the monitoring structure of the present invention, and the position and the orientation of slip surfaces and the evolution process thereof can be monitored, and the accuracy and sensitivity of monitoring can be improved.

2. Different embedment manners are selected according to different application scenarios, thus being more conducive to improvement in sensitivity of monitoring.

BRIEF DESCRIPTION OF THE DRAWINGS

The drawings accompanying the description that constitute a part of the present disclosure are meant to provide a further understanding of the present application. Exemplary embodiments of the present application and descriptions thereof are meant to explain the present application and not intended to be improper limiting of the present application.

Figure 1:
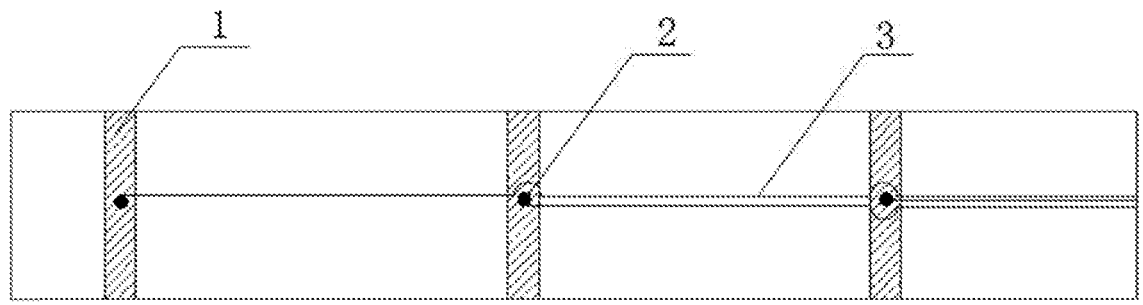
FIG. 1 is a schematic diagram of arrangement of a smart geosynthetic material and a lead.

Reference numerals: 1, conductive adhesive, 2, measuring point, 3, lead, 4, geogrid, 5, heat shrinkable tube, 6, data acquisition instrument, 7, strip-shaped smart geosynthetic material compound device, 8, mortar or slurry filled gap, 9, subgrade or slope, and 10, predicted slip surface.

DETAILED DESCRIPTION OF THE EMBODIMENTS

It should be pointed out that the following detailed descriptions are all exemplary and intended to provide further illustration of the present application. Unless stated otherwise, all technical and scientific terms used herein have the same meanings as commonly understood by those of ordinary skill in the art to which the present application belongs.

It needs to be noted that the terms used herein is merely meant to describe specific embodiments and not intended to limit exemplary embodiments according to the present application. As used herein, the singular forms are intended to include the plural forms as well, unless otherwise clearly stated in the context. In addition, it should be also understood that the terms "comprising" and/or "including", when used in this description, are taken to specify the presence of stated features, steps, operations, devices, components and/or combinations thereof.

Figure 4:
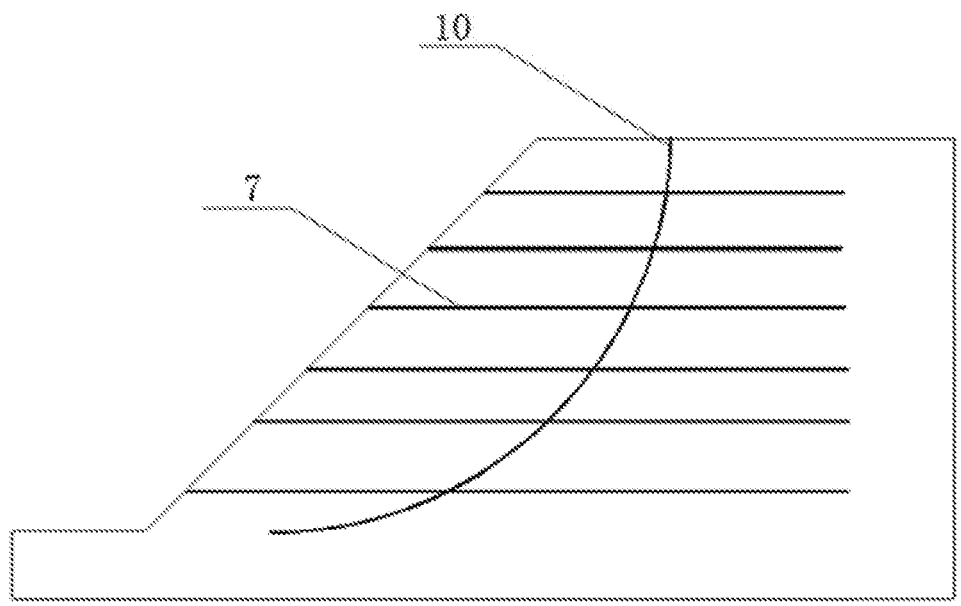
FIG. 4 is a structural schematic diagram of the smart geosynthetic material when transversely arranged.
Figure 6:
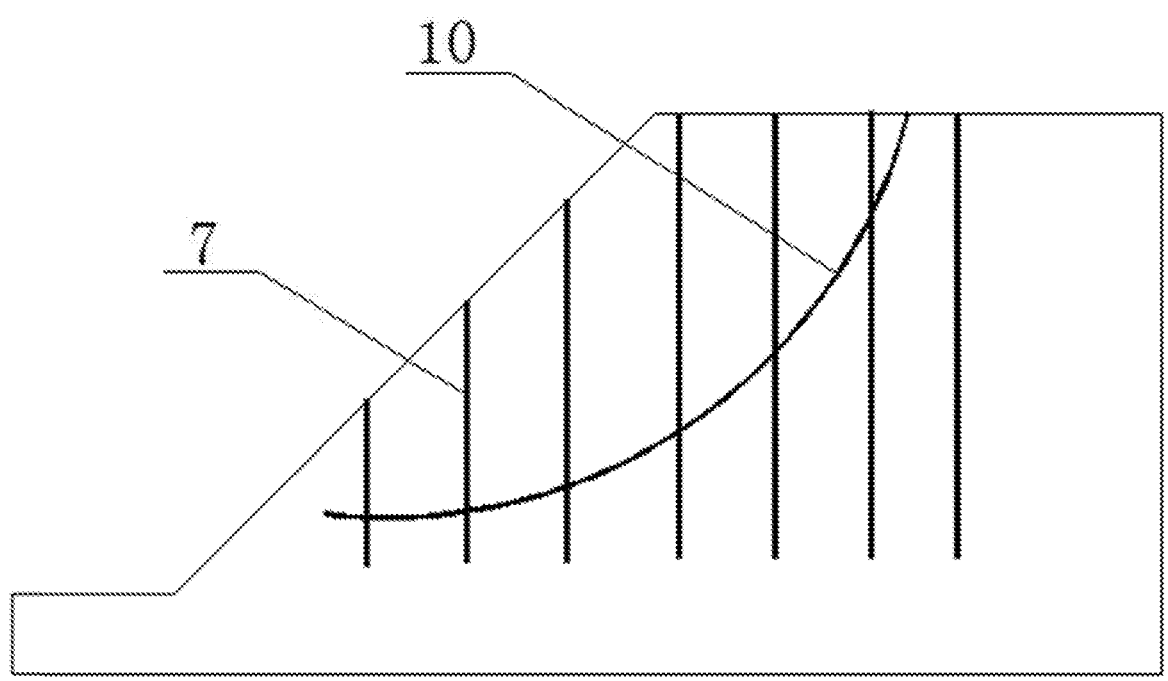
FIG. 6 is a structural schematic diagram of the smart geosynthetic material when vertically arranged.

As shown in FIG. 4 and FIG. 6, a structure for monitoring the stability of an existing subgrade/slope comprises a subgrade or slope 9 to be monitored and a plurality of strip-shaped smart geosynthetic material compound devices 7.

Figure 3:
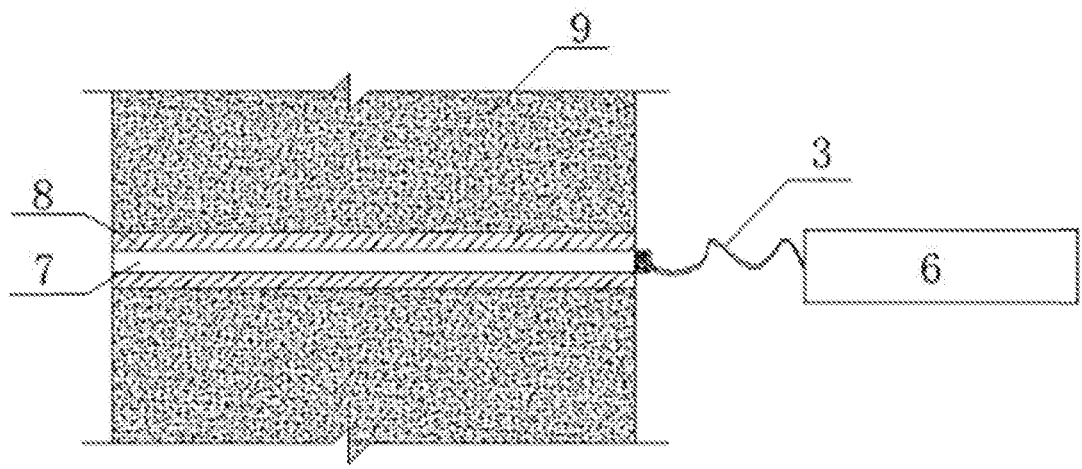
FIG. 3 is a sectional diagram of the smart geosynthetic material when transversely arranged.
Figure 5:
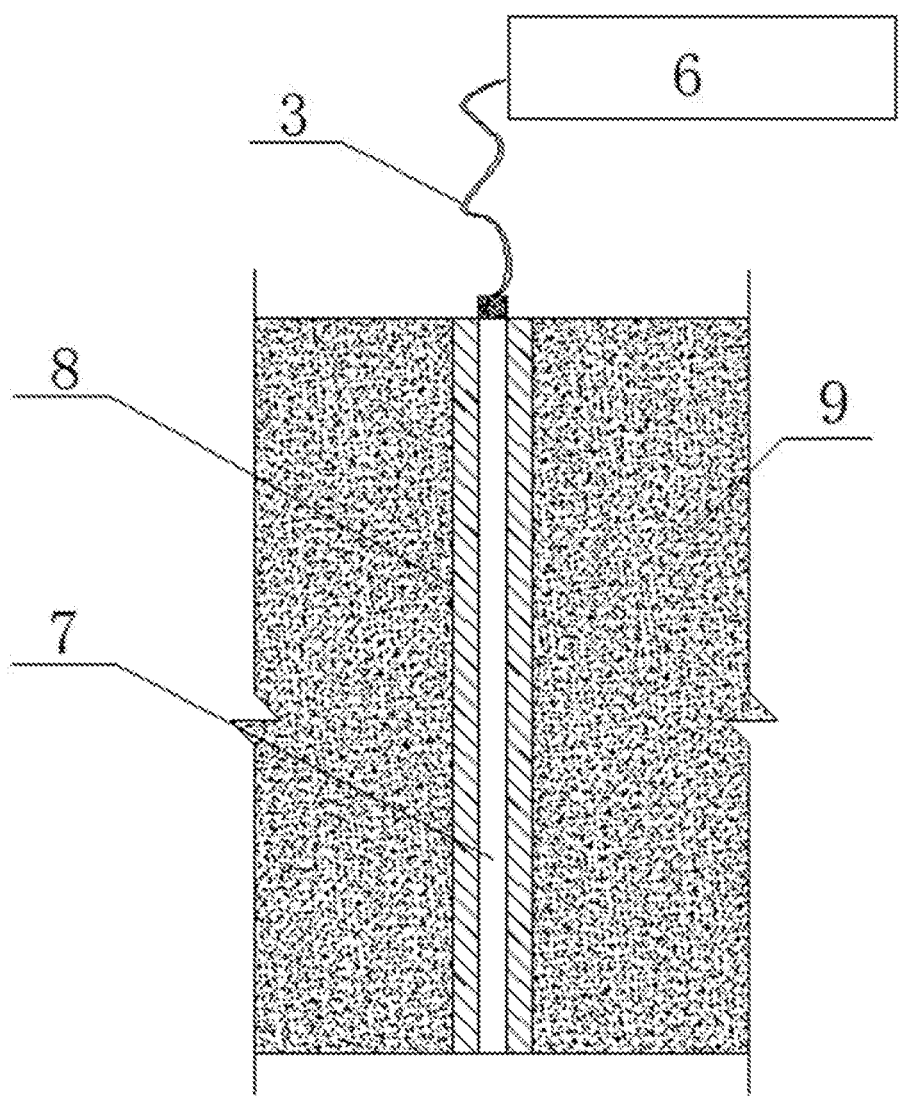
FIG. 5 is a sectional diagram of the smart geosynthetic material when vertically arranged.

A plurality of vertical boreholes are drilled in a width direction of the subgrade or slope 9, or a plurality of transverse boreholes are drilled in a vertical direction thereof. A distance between every two adjacent boreholes is 1-2 m, preferably 1-1.5 m, and more preferably 1 m. As shown in FIG. 3 and FIG. 5, the diameter of each borehole is 8-15 cm, preferably 8-10 cm, and more preferably 10 cm. One strip-shaped smart geosynthetic material compound device 7 is buried in each vertical borehole or transverse borehole so deep as to run through a predicted slip crack surface 10 of the subgrade or slope. A gap between the strip-shaped smart geosynthetic material compound device 7 and the inner wall of the borehole is filled tightly so that the force environment of the strip-shaped smart geosynthetic material compound device 7 is close to the internal environment of the subgrade or slope 9.

Figure 2:
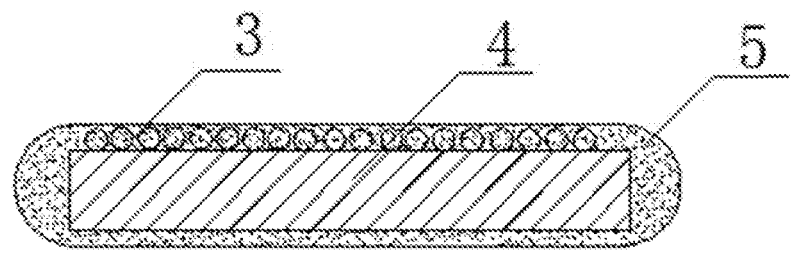
FIG. 2 is a schematic sectional diagram of a smart geosynthetic material.

As shown in FIG. 1 and FIG. 2, the strip-shaped smart geosynthetic material compound device 7 comprises a geogrid 4, a lead 3, and a heat shrinkable tube 5. The geogrid 4 is strip-shaped. The lead is arranged in a length direction of the geogrid 4, and the lead 3 and the geogrid 4 are fixedly connected at an interval of a set distance, with each fixed point forming a measuring point. A distance between every two adjacent measuring points is 0.5-1 m, preferably 0.7-1 m, and more preferably 1 m. The lead 3 and the geogrid 4 are bonded by a conductive adhesive 1 and fixed using an adhesive tape at each measuring point 2, and each measuring point 2 is fixed in a middle position of the geogrid 4. The lead 3, before being fixed, should be pulled tight. When the lead 3 is pulled tight, the geogrid 4 may become deformed under a force, and the lead 3 may become deformed accordingly, providing better detection sensitivity. The geogrid 4 is wrapped in the heat shrinkable tube 5, and a free end of the lead 3 is drawn out of the heat shrinkable tube 5. The heat shrinkable tube 5 contains an adhesive and is of a double-layer structure with an outer layer made from a polyolefin alloy material and an inner layer made from a hot melt adhesive. After the lead 3 is fixed to the geogrid 4, the geogrid 4 and the lead 3 are wrapped in the adhesive-containing heat tube. After being heated to 84-120° C., the adhesive-containing heat tube may shrink, and the hot melt adhesive of the inner layer is melted so that the geogrid 4 and the lead 3 are wrapped therein tightly.

The specific construction process will be described below.

Horizontal Embedment: Suitable for a High Roadbed and a High Slope

1. Boreholes each having the diameter of 10 cm are dilled transversely in the subgrade or slope, and each borehole is required to be wider than a predicted slip crack surface of the subgrade or slope. The boreholes may be drilled in the vertical direction at intervals of 1 m to 2 m.

2. A smart geosynthetic material is nested into a plastic tube and then fed into each borehole until reaching the bottom of the borehole. As the smart geosynthetic material is strip-shaped, it should be ensured that the strip, when transversely put into the borehole, is perpendicular to the force direction.

3. A gap in each borehole is filled. During gap filling, the plastic tube is slowly taken out. The plastic tube may be taken out a distance of about 2 m once the gap is filled by about 2 m, until the gap is completely filled. In this process, it should be ensured that the bottom of the plastic tube is immersed in fillers. To enable the surrounding force environment of the geosynthetic material to be close to the original environment, different materials may be selected to fill gaps with respect to different soil slopes. For soft rock or decomposed rock slopes, gaps therein may be filled with M20 cement mortar having a cement-mortar ratio of 1:1 by using a pressure grouting machine. For hard rock slopes, gaps therein may be filled with M30 cement mortar having a cement-mortar ratio of 1:1 by using a pressure grouting machine. For soft soil slopes, gaps therein may be filled with bentonite slurry. The bentonite slurry may contain water, bentonite, alkali, and cellulose in a mixture ratio of water: bentonite: alkali: cellulose=1000:(60-100):(2-5):(2-5) (mass ratio), preferably the ratio of water: bentonite: alkali: cellulose=1000:(80-100):(3-5):(3-5) (mass ratio), more preferably the ratio of water: bentonite: alkali: cellulose=1000: (80-90): (3-4):(3-4) (mass ratio), and most preferably the ratio of water: bentonite: alkali: cellulose=1000:85:4:4 (mass ratio). For hard soil slopes, gaps therein may be filled with cement soil, where bentonite selected as soil and cement P·C32.5 are used, with a mixed cement ratio of 10%-15% and a water-cement ratio of 1 in cement slurry. Outside the borehole, the opening of the borehole is sealed with mortar.

4. A lead of the smart geosynthetic material is drawn out, and the lead is connected to a data acquisition instrument. A resistance value at each measuring point is measured. Two adjacent measurement points with the maximal resistance difference are found out, thereby the position and the orientation of the slip crack surface of soil mass and the evolution process of the slip crack surface can be analyzed and determined.

Vertical Embedment: Suitable for a Wide Subgrade and a Wide Slope

1. Boreholes each having the diameter of 10 cm are dilled vertically in the subgrade or slope, and each borehole is required to be so deep as to run through a predicted slip crack surface of the subgrade or slope. The boreholes may be drilled in a width direction of the subgrade or slope at intervals of 1 m to 2 m.

2. A smart geosynthetic material is nested into a plastic tube and then fed into each borehole until it reaches the bottom of the borehole. As the smart geosynthetic material is strip-shaped, it should be ensured that the strip, when vertically put into the borehole, is perpendicular to the force direction.

3. A gap in each borehole is filled. During gap filling, the plastic tube is slowly taken out. The plastic tube may be taken out a distance of about 2 m once the gap is filled by about 2 m, until the gap is completely filled. In this process, it should be ensured that the bottom of the plastic tube is immersed in fillers. To enable the surrounding force environment of the geosynthetic material to be close to the original environment, different materials may be selected to fill gaps with respect to different soil slopes. For soft rock or decomposed rock slopes, gaps therein may be filled with M20 cement mortar having a cement-mortar ratio of 1:1 by using a pressure grouting machine. For hard rock slopes, gaps therein may be filled with M30 cement mortar having a cement-mortar ratio of 1:1 by using a pressure grouting machine. For soft soil slopes, gaps therein may be filled with bentonite slurry. The bentonite slurry may contain water, bentonite, alkali, and cellulose in a mixture ratio of water: bentonite: alkali: cellulose=1000:(60-100):(2-5):(2-5) (mass ratio), preferably a ratio of water: bentonite: alkali: cellulose=1000:(80-100):(3-5):(3-5) (mass ratio), more preferably a ratio of water: bentonite: alkali: cellulose=1000:(80-90):(3-4):(3-4) (mass ratio), and most preferably a ratio of water: bentonite: alkali: cellulose=1000:85:4:4 (mass ratio). For hard soil slopes, gaps therein may be filled with cement soil, where bentonite selected as soil and cement P·C32.5 are used, with a cement ratio of 10%-15% (mass percentage), preferably 10%-13% (mass percentage), and more preferably 13% (mass percentage). In addition, the mass ratio of water to bentonite in slurry is 1:1. Outside the borehole, the opening of the borehole is sealed with mortar.

4. A lead in the smart geosynthetic material is drawn out to be connected to a data acquisition instrument. A resistance value at each measuring point is measured. Two adjacent measurement points with the maximal resistance difference are found out, thereby the position and the orientation of the slip crack surface of soil mass and the evolution process of the slip crack surface can be analyzed and determined.. The foregoing is merely descriptions of preferred embodiments of the present application and not intended to limit the present application. For those skilled in the art, various changes and variations can be made to the present application. Any modifications, equivalent substitutions and the like made without departing from the spirit and the principles of the present application shall be encompassed in the scope of protection of the present application.

The invention claimed is:

1. A structure for monitoring the stability of an existing subgrade/slope, comprising:
   a subgrade or slope to be monitored and a plurality of strip-shaped smart geosynthetic material compound devices,
   wherein a plurality of vertical boreholes are drilled in a width direction of the subgrade or slope, or a plurality of transverse boreholes are drilled in a vertical direction thereof; one strip-shaped smart geosynthetic material compound device is buried in each vertical borehole or transverse borehole so deep as to run through a predicted slip crack surface of the subgrade or slope; a gap between the strip-shaped smart geosynthetic material compound device and the inner wall of the borehole is filled tightly so that the force environment of the strip-shaped smart geosynthetic material compound device is close to the internal environment of the subgrade or slope;
   each strip-shaped smart geosynthetic material compound device comprises a geogrid, a lead, and a heat shrinkable tube; the geogrid is strip-shaped; the lead is arranged in a length direction of the geogrid, and the lead and the geogrid are fixedly connected at an interval of a set distance, with each fixed point forming a measuring point; the geogrid is wrapped in the heat shrinkable tube, and a free end of the lead is drawn out of the heat shrinkable tube.

2. The monitoring structure according to claim 1, wherein the lead and the geogrid are bonded by a conductive adhesive and fixed using an adhesive tape at each measuring point.

3. The monitoring structure according to claim 1, wherein a distance between every two adjacent measuring points is 0.5-1 m.

4. The monitoring structure according to claim 1, wherein each measuring point is fixed in a middle position of the geogrid.

5. The monitoring structure according to claim 1, wherein the lead between every two adjacent measuring points is pulled tight.

6. The monitoring structure according to claim 1, wherein the heat shrinkable tube contains an adhesive and is of a double-layer structure with an outer layer made from a polyolefin alloy material and an inner layer made from a hot melt adhesive.

7. The monitoring structure according to claim 1, wherein a distance between every two adjacent boreholes is 1-2 m; and the diameter of each borehole is 8-15 cm.

* * * * *